United States Patent [19]

Tobin

[11] 4,038,331

[45] July 26, 1977

[54] CATALYTIC PROCESS FOR PREPARATION OF PERFLUOROALKYL SUBSTITUTED AROMATIC COMPOUNDS

[75] Inventor: John H. Tobin, Beacon Falls, Conn.

[73] Assignee: Olin Corporation, New Haven, Conn.

[21] Appl. No.: 643,227

[22] Filed: Dec. 22, 1975

Related U.S. Application Data

[63] Continuation-in-part of Ser. No. 549,589, Feb. 13, 1975, abandoned.

[51] Int. Cl.$^2$ ............................................. C07C 25/14
[52] U.S. Cl. ........................... 260/651 F; 260/250 R; 260/250 A; 260/250 B; 260/250 P; 260/251 R; 260/251 Q; 260/283 R; 260/290 HL; 260/296 N; 260/296 H; 260/465 G; 260/651 HA
[58] Field of Search ....... 260/651 F, 651 HA, 465 G, 260/290 HL, 283 R, 650 F, 649 F, 64.8 F

[56] References Cited

U.S. PATENT DOCUMENTS

| | | | |
|---|---|---|---|
| 3,190,825 | 6/1965 | Huyser | 260/651 F |
| 3,271,441 | 9/1966 | Brace | 260/651 F |
| 3,318,963 | 5/1967 | Pass | 260/651 F |
| 3,408,411 | 10/1968 | McLoughlin et al. | 260/651 F |
| 3,742,074 | 6/1973 | Hermann et al. | 260/651 F |
| 3,917,725 | 11/1975 | Haszeldine et al. | 260/651 F |

OTHER PUBLICATIONS

Tiers, *J. AM. Chem. Soc.* 82 5513 (1960).

*Primary Examiner*—C. Davis
*Attorney, Agent, or Firm*—William A. Simons; F. A. Iskander; Thomas P. O'Day

[57] ABSTRACT

Perfluoroalkyl substituted aromatic or heteroaromatic compounds are prepared by reacting a perfluoroalkyl bromide with an aromatic compound in the vapor phase in the presence of a catalytic amount of iodine or an iodine generating compound.

9 Claims, No Drawings

CATALYTIC PROCESS FOR PREPARATION OF PERFLUOROALKYL SUBSTITUTED AROMATIC COMPOUNDS

RELATED APPLICATION

The present application is a continuation-in-part of copending U.S. patent application Ser. No. 549,589, filed Feb. 13, 1975, now abandoned.

BACKGROUND OF THE INVENTION

This invention is directed to a method for preparing perfluoroalkyl substituted aromatic compounds. More particularly, the invention is directed to a method for preparing such compounds by reacting a perfluoroalkyl bromide with an aromatic compound in the presence of a catalytic amount of iodine or an iodine generating compound such as trifluoromethyl iodide.

Perfluoroalkyl aromatic compounds are commercially prepared by reacting a perfluoroalkyl iodide with the aromatic compound. British Patent 840,725 describes such a process wherein one mole of the aromatic compound is heated with two moles of the perfluoroalkyl iodide. This process is wasteful of one mole of the iodide in that two moles of perfluoroalkyl iodide are employed to produce each mole of product.

U.S. Pat. No. 2,957,031 describes a process for reacting perfluoro acid halides with aromatic compounds in the presence of nickel carbonyl. The highly toxic nature of nickel carbonyl makes the process commercially unacceptable.

Huyser, Earl S. and Bedard, Ernest, *J. Org. Chem* 29, 1588 (1964) indicates that the mechanism by which perfluoroalkylation occurs with the aromatic ring involves the formation of a perhaloalkyl free radical which then attacks the aromatic ring. In recognition of this mechanism, U.S. Pat. No. 3,271,441 discloses a process in which the ratio of perfluoroalkyl iodide to aromatic compound is reduced to about 1 by conducting the reaction in the presence of a free radical generating compound selected from the group consisting of organic peroxides and aliphatic azo compounds.

While perhaloalkyl iodides have been used commercially to prepare perfluoroalkyl aromatics, efforts to utilize perfluoroalkyl bromides have been unsuccessful. As shown in copending U.S. patent application Ser. No. 424,394, now U.S. Pat. No. 3,890,326, the uncatalyzed vapor phase reaction of an aromatic compound and trifluoromethyl bromide produces bromine substitution, thus, producing fluoroform and brominated aromatic products to the virtual exclusion of perhaloalkyl substituted aromatics.

SUMMARY OF THE INVENTION

It has now been found, however, that perfluoroalkyl substituted aromatic compounds may be prepared from less expensive perhaloalkyl bromides by reacting a perhaloalkyl bromide with an aromatic compound in the vapor phase and under anhydrous conditions in the presence of a catalytic amount of iodine or an iodine generating compound such as trifluoromethyl iodide.

DESCRIPTION OF THE INVENTION

In its broadest aspect, the invention comprises heating together in the vapor phase and under anhydrous conditions and at a temperature in the range of 300° – 800° C. an aromatic compound having at least one nuclear hydrogen and a perfluoroalkyl bromide in the presence of a catalytic amount of iodine or an iodine generating compound.

A number of aromatic compounds will undergo perfluoroalkylation in accordance with the present invention as long as the aromatic nucleus is provided with at least one nuclear carbon-substituted hydrogen atom which is available for perfluoroalkylation. As used herein, the term aromatic compound means an aromatic hydrocarbon, a heteroaromatic compound having 1–2 ring nitrogen atoms, balance being carbon atoms, or a substituted derivative thereof which does not contain substituents other than hydrogen which are easily alkylated. The substituted aromatic compounds must have at least one ring substituted hydrogen and may, in addition, contain such substituents as perhaloalkyl, halogen and nitrile. Reactants substituted with such reactive groups as hydroxyl, alkoxyl, nitro, amino, carboxyl, aldehyde, or partly substituted alkyl or alkenyl may not advantageously be employed in the process since reaction with the substituent will occur.

The aromatic hydrocarbons useful in the present process are suitably aromatic compounds having 6–10 ring carbon atoms. An aromatic hydrocarbon having a single 6-membered ring such as benzene or substituted benzene is preferred but the aromatic hydrocarbon may also be an unsubstituted or appropriately substituted multi-ring hydrocarbon such as naphthalene. The preferred aromatic reactant may thus be benzene, a halobenzene, perhaloalkyl benzene, a benzonitrile or a benzoid reactant substituted with a mixture of halogen, perhaloalkyl and nitrile substituents. Suitably from 0 to about 5 of such substituents, preferably 0–3, may be present as long as at least one ring substituted hydrogen is present on a ring carbon atom.

Likewise, the heteroaromatic compound is suitably one having 6–10 ring atoms consisting of 1–2 atoms, preferably 1, of nitrogen, the balance being carbon. A heteroaromatic compound having a single 6-membered ring containing one ring nitrogen atom, such as pyridine or substituted pyridine is preferred, but the heteroaromatic may also be an unsubstituted or appropriately substituted pyridazine, pyrimidine, or pyrazine or a more complex ring structure such as quinoline, isoquinoline, quinazoline, quinoxaline, phthalazine, naphthyridine or a pyridopyridine.

The selected heteroaromatic reactant may be unsubstituted, i.e. hydrogen only, or be substituted with substituents selected from the group consisting of halogen, perhaloalkyl or nitrile or a combination of such substituents. Thus, the preferred aromatic reactant is pyridine, halopyridine, perhaloalkylpyridine, nitrilopyridine or a pyridine nucleus substituted with a mixture of halogen, perhaloalkyl and nitrile substituents. Suitably 0–5 such substituents, preferably 0–3, may be present as long as at least one ring substituted hydrogen atom is present on a ring carbon atom.

Halogen substituents may be the same or different halogens as desired and may include chlorine, bromine, fluorine or combinations thereof. Thus, the preferred reactant may be, for example, fluorobenzene, bromochlorobenzene, dibromobenzene, difluorobenzene, fluorochlorobenzene and comparably substituted pyridines.

Perhaloalkyl groups may also be present on the ring of the starting aromatic compound, suitably, those in which the alkyl component has 1–16 carbon atoms, advantageously 1–8 carbon atoms, preferably a lower alkyl having 1–4 carbon atoms. Typical, substituents include $CF_3$, $C_2F_5$, $CCl_3$, etc. While the most common halogens on the alkyl group are fluorine and chlorine, bromine may also be used as may a combination thereof. The principal criteria is that hydrogens on the alkyl side chain must all be replaced to avoid side chain substitution.

A nitrile group or a nitrile in combination with one or more halogen substituents or one or more perhaloalkyl substituents or combinations thereof may also be present on the aromatic compound.

The second is a perfluoroalkyl bromide in which the alkyl component has from 1–6 carbon atoms, suitably 1–8 carbons, advantageously 1–4 carbon atoms. The preferred compound is trifluoromethyl bromide. Advantageously about 1 mole, suitably 0.5–2.0 moles, of perfluoroalkyl bromide are employed per mole of aromatic reactant.

The novel feature of the present invention resides in the use of an appropriate catalyst. In the prior application, referred to above, it was disclosed that the uncatalyzed vapor phase reaction of trifluoromethyl bromide with an aromatic compound produced a brominated aromatic compound. Virtually, no haloalkylation occurred. Surprisingly, however, when the reaction is conducted in the presence of a catalytic amount of iodine or an iodine generating compound perhaloalkylation occurs.

Suitable iodine generating compounds which may be used in lieu of iodine include these compounds which decompose at a temperature in the range of 300°–800° C. to form iodine in situ. These include inter alia, perhaloalkyl iodines having 1–4 carbons, and interhalogen compounds. For example, one may utilize a perfluoroalkyl iodide, advantageously a lower perfluoroalkyl iodide having 1–4 carbons, preferably trifluoromethyl iodide, or iodine containing interhalogens such as IBr, ICl.

In accordance with the present invention, the reactants and catalyst are charged to a vapor phase reactor maintained at a temperature in the range of 300°–800° C. which has been previously purged with nitrogen or HCl to remove water vapor, preferably 400°–700° C. and the reaction is permitted to proceed under anhydrous conditions in accordance with the generalized reaction.

wherein $R_f$ represents a perfluoroalkyl moiety, Ar—H represents an aromatic compound having an available ring hydrogen and [I] represents iodine or an iodine generating compound, all as described above. By-products II and III are readily separated and serve as starting materials for other chemicals.

In conducting the reaction a low mole ratio of iodine or iodine generating compound to aromatic compound is utilized, suitably in the range of 1:250 to 1:10, preferably in the range of 1:100 to 1:20. The precise upper and lower limits may be varied considerably within this range and even exceed it on the high side if desired. On the low side a catalytic amount of iodine or iodine generating compound must be present. The high side of the ratio is dictated by economic considerations and is, therefore, not a critical feature of the invention.

The reaction is allowed to proceed for a period of at least 1 minute up to several (6–10) hours depending on the temperature, the specific reactants which have been selected and on the degree of completion required for the reaction. The optimum residence in the reactor is readily determined by those skilled by simply varying the residence time for a particular system while keeping temperature constant.

EXAMPLE 1

A vapor phase reactor was constructed of quartz and consisted of three sections. Section I was a series of valves permitting the introduction of one or two gases and a liquid in measured quantities. Section II was a reactor tube 24 inches long and 1 inch in diameter and packed with an inert support. Section III is a trap system to trap product using a cold finger filled with ice water.

The reaction tube was heated to 550°–570° C. under a nitrogen purge. The nitrogen was shut off and 17g benzene and 22g trifluoromethyl bromide were introduced into the reaction tube over a period of 17 minutes.

Product collected from the trap and analyzed by vapor phase chromatography and infrared spectroscopy comprised: benzene 75.9 percent by weight, bromobenzene 22.2 percent by weight, miscellaneous brominated benzenes 1.8 percent by weight.

This example demonstrates the uncatalyzed reaction of a perfluoroalkyl bromide with an aromatic compound and confirms that in the absence of a catalyst no halomethylation of the aromatic ring occurs. Only brominated products could be detected.

EXAMPLES 2–6

A 1 × 24 quartz tube filled with inert packing was heated to the desired temperature under a nitrogen purge. When the temperature stabilized nitrogen flow was stopped and reactants introduced. Products were collected in a trap cooled to −30° C. with an ice/alcohol bath. The trapped products were analyzed by vapor phase chromatography, infrared spectroscopy and mass spectroscopy.

Temperatures residence time, reactant amounts, and yields based on aromatic compound converted are presented in Table I.

TABLE I

| EXAMPLE | TEMP. °C | TIME (Min.) | REACTANTS (mol) | | | | YIELD (%) OCF$_3$ |
|---|---|---|---|---|---|---|---|
| | | | CF$_3$I | I$_2$ | CF$_3$Br | OH | |
| 2 | 500 | 6.0 | .002 | | .14 | .20 | 11.1 |
| 3 | 600 | 5.0 | .005 | | .12 | .19 | 40.0 |
| 4 | 600 | 5.2 | .005 | | .13 | .19 | 45.0 |
| 5 | 700 | 5.0 | .005 | | .13 | .19 | 41.7 |
| 6 | 550–600 | 10.0 | | .003 | .168 | .121 | 58.3 |

EXAMPLE 7

A 1000 ml Hasteloy B reactor was charged with 400g benzene and 0.449 mol di-t-butylperoxide, sealed and charged to 230 psig and 0.4–0.5 mol trifluoromethyl bromide added. The reactor was heated to 140° C. for 8 hours when allowed to cool and vented. A total of 477.7g was removed from the reactor and analyzed by vapor phase chromatography yield of benzotrifluoride was 13.9%.

This example demonstrates that even with free radical generating compounds present the reaction of perfluoroalkyl bromides with aromatic compounds produces unsatisfactory yields. Thus that which may have been a suitable solution for iodides clearly does not work for the bromide system.

Furthermore, the di-t-butylperoxide was used up in the reaction and was, therefore, not recoverable whereas the catalyst of the present invention is completely recoverable.

EXAMPLE 8

A solution of 1.0g (0.008g atom) iodine per 99.0g (1.03 mole) fluorobenzene was passed into a quartz tubular reactor which had been purged with HCl and nitrogen at a rate of 40–50 ml/hr. Simultaneously, trifluoromethyl bromide was introduced at a rate of 2.5–3.0g/min. The temperature of the reactor was 650°–700° C. Fluorobenzotrifluoride yield based on aromatic compound conversion was 16%.

I claim:

1. A process for preparing perfluoroalkyl substituted aromatic compounds which comprises:
   A. heating together in the vapor phase under anhydrous conditions at a temperature of 300°–800° C
      1. an aromatic hydrocarbon, said aromatic hydrocarbon being substituted with at least one atom of hydrogen and 0–3 further substituents selected from the group consisting of halogen, perhaloalkyl having 1–4 carbons, nitrile and combinations of such further substituents,
      2. a perfluoroalkyl bromide having 1–16 carbon atoms, and
      3. a catalytic amount of a catalyst selected from the group consisting of iodine and an iodine generating compound selected from the group consisting of perhaloalkyl iodine having 1–4 carbons; and
   B. recovering said perfluoroalkyl substituted aromatic compound.

2. The process of claim 1 wherein said aromatic compound is selected from the group consisting of benzene, a halobenzene, perhaloalkyl benzene, a benzonitrile and a benzoid reactant substituted with a mixture of halogen, perhaloalkyl and nitrile substituents.

3. The process of claim 2 wherein said aromatic compound is benzene.

4. The process of claim 1 wherein said perfluoroalkyl bromide has 1–8 carbon atoms.

5. The process of claim 4 wherein said perfluoroalkyl bromide is trifluoromethyl bromide.

6. The process of claim 1 wherein said catalyst is iodine.

7. The process of claim 1 wherein said catalyst is a lower perfluoroalkyl iodide having 1–4 carbon atoms.

8. The process of claim 7 wherein said catalyst is trifluoromethyl iodide.

9. The process of claim 1 wherein said aromatic compound is benzene, said perfluoroalkyl bromide is trifluoromethyl bromide, said catalyst is iodine and said temperature is 400°–700° C.

* * * * *

UNITED STATES PATENT OFFICE
CERTIFICATE OF CORRECTION

Patent No. 4,038,331            Dated July 26, 1977

Inventor(s) John H. Tobin

It is certified that error appears in the above-identified patent and that said Letters Patent are hereby corrected as shown below:

Column 3, line 11, after "second" insert --reactant--.

Column 3, line 12, "1-6" should read --1-16--.

Column 3, line 29, "these" should read --those--.

Column 4, line 39, "1 x 24" should read --1" x 24"--.

Column 4, in Table I, the heading "OH" should read --ØH--.

Column 4, in Table I, the heading "OCF$_3$" should read --ØCF$_3$--.

Column 4, line 67, "when" should read --then--.

*Signed and Sealed this*

*Fourteenth* Day of *February 1978*

[SEAL]

Attest:

RUTH C. MASON        LUTRELLE F. PARKER
*Attesting Officer*      *Acting Commissioner of Patents and Trademarks*